United States Patent
Kaneda

(10) Patent No.: US 12,327,621 B2
(45) Date of Patent: Jun. 10, 2025

(54) REPORTING DEVICE, REPORTING METHOD, REPORTING PROGRAM, AND REPORTING SYSTEM

(71) Applicant: Spinshell, Inc., Tokyo (JP)

(72) Inventor: Hiroshi Kaneda, Tokyo (JP)

(73) Assignee: Spinshell, Inc., Tokyo (JP)

(*) Notice: Subject to any disclaimer, the term of this patent is extended or adjusted under 35 U.S.C. 154(b) by 431 days.

(21) Appl. No.: 17/630,271

(22) PCT Filed: Jul. 30, 2020

(86) PCT No.: PCT/JP2020/029205
§ 371 (c)(1),
(2) Date: Jan. 26, 2022

(87) PCT Pub. No.: WO2021/020498
PCT Pub. Date: Feb. 4, 2021

(65) Prior Publication Data
US 2022/0336070 A1    Oct. 20, 2022

Related U.S. Application Data

(60) Provisional application No. 62/880,659, filed on Jul. 31, 2019.

(51) Int. Cl.
*G16H 15/00* (2018.01)

(52) U.S. Cl.
CPC .................. *G16H 15/00* (2018.01)

(58) Field of Classification Search
CPC ........ G16H 15/00; G16H 30/20; G16H 30/40; G16H 40/67; G16H 50/70; G16H 80/00; G16H 50/20
See application file for complete search history.

(56) References Cited

U.S. PATENT DOCUMENTS

2014/0180711 A1* 6/2014 Kamen ................. G16H 40/63
                                                                    705/2
2017/0300664 A1   10/2017 Matsuki
(Continued)

FOREIGN PATENT DOCUMENTS

IN    1279MU2014 A    10/2015
JP    2012-519003      8/2012
(Continued)

OTHER PUBLICATIONS

Duffy et al. ("Glyph-Based Video Visualization for Semen Analysis," in IEEE Transactions on Visualization and Computer Graphics, vol. 21, No. 8, pp. 980-993, Aug. 2015, doi: 10.1109/TVCG.2013.265) (Year: 2015).*

(Continued)

*Primary Examiner* — Chad A Newton
(74) *Attorney, Agent, or Firm* — Ballard Spahr LLP

(57) ABSTRACT

A reporting device is described that includes a moving image receiving unit configured to receive a moving image obtained by imaging sperm of a user from a user terminal, a moving image processing unit configured to display the moving image received by the moving image receiving unit on an embryologist terminal, a report information receiving unit configured to receive, from the embryologist terminal, report information indicating a result obtained by analyzing the sperm of the user by an embryologist, based on the moving image displayed on the embryologist terminal, and a report information processing unit configured to display the report information received by the report information receiving unit on the user terminal.

2 Claims, 8 Drawing Sheets

(56) References Cited

U.S. PATENT DOCUMENTS

| | | | |
|---|---|---|---|
| 2019/0265223 A1* | 8/2019 | Irisawa | C12N 5/061 |
| 2021/0041336 A1* | 2/2021 | Barnea | G16H 50/70 |
| 2021/0158521 A1* | 5/2021 | Shaked | G06T 7/0012 |
| 2021/0270717 A1* | 9/2021 | Sun | C12N 5/061 |

FOREIGN PATENT DOCUMENTS

| | | |
|---|---|---|
| JP | 6045738 B | 12/2016 |
| JP | 2018-530851 A | 10/2018 |
| WO | WO 2010/099468 A2 | 9/2010 |
| WO | WO 2017/070253 A1 | 4/2017 |
| WO | WO 2017/154974 A1 | 9/2017 |
| WO | WO 2018/140999 A1 | 8/2018 |
| WO | WO 2019/131254 A1 | 7/2019 |

OTHER PUBLICATIONS

International Search Report was mailed on Oct. 27, 2020 by the International Searching Authority for International Application No. PCT/JP2020/029205 filed on Jul. 31, 2019 and published as WO 2021/020498A1 (Applicant—Spinshell, Inc.) (4 pages).
Chinese Office Action and Search Report issued in related application No. CN202080051031.3 mailed Nov. 23, 2024.

\* cited by examiner

FIG. 3

SPERM CHECK REPORT — 50

UPLOAD DATE MM DD, YYYY
SERIAL CODE ZZZZZZZZZZ — A1

A2

MOVING IMAGE 1
COLLECTION DATE MM DD, YYYY
SEMEN AMOUNT ABOUT 1.0ml
SPERM CONCENTRATION ABOUT 45 MILLION/ml
SPERM MOTILITY RATE ABOUT 40%
TOTAL SPERM COUNT ABOUT 45 MILLION
TOTAL MOTILE SPERM COUNT ABOUT 18 MILLION — A2-1

MOVING IMAGE 2
COLLECTION DATE MM DD, YYYY
SEMEN AMOUNT ABOUT 1.4ml
SPERM CONCENTRATION ABOUT 45 MILLION/ml
SPERM MOTILITY RATE ABOUT 70%
TOTAL SPERM COUNT ABOUT 63 MILLION
TOTAL MOTILE SPERM COUNT ABOUT 44 MILLION/ml — A2-2

OVERALL FINDINGS
YOU CAN EXPECT A NATURAL PREGNANCY. — A3

COMMENTS AND ADVICE
ALL ITEMS SATISFY THE WHO REFERENCE VALUES. SINCE THE WHO REFERENCE MEANS THE LOWEST VALUE AT WHICH A NATURAL PREGNANCY CAN BE EXPECTED, IT IS DESIRABLE THAT THERE IS A LITTLE MORE SEMEN AMOUNT TO INCREASE THE PROBABILITY OF A NATURAL PREGNANCY. — A4

REPORTING DEVICE, REPORTING METHOD, REPORTING PROGRAM, AND REPORTING SYSTEM

CROSS-REFERENCE TO RELATED APPLICATIONS

This application is a U.S. National Phase Application of International Application No. PCT/JP2020/029205, filed Jul. 30, 2020, which claims priority to U.S. Provisional Application No. 62/880,659, filed Jul. 31, 2019, each of which are hereby incorporated by reference in their entirety.

Priority is claimed on U.S. provisional application 62/880,659, filed in the United States on Jul. 31, 2019, the content of which is incorporated herein by reference.

TECHNICAL FIELD

The present disclosure relates to a reporting device, a reporting method, a reporting program, and a reporting system.

BACKGROUND ART

In recent years, the number of men and women suffering from infertility is increasing due to factors such as late marriage, advanced maternal age, and changes in lifestyle. As one of the causes of infertility, abnormality in male sperm is an exemplary example. A test for sperm abnormality can be performed at a specialized medical institution. In order to test sperm, it is necessary to collect sperm and submit the collected sperm to the hospital. Further, sperm testing is time consuming and costly. Therefore, the sperm test cannot be easily performed, and the detection of sperm abnormality may be delayed. Therefore, various techniques have been proposed that allow a sperm test to be easily performed at home or the like.

For example, Patent Document 1 below discloses a technique in which when a sperm moving image is captured by a camera of a smartphone by using a tool capable of capturing a magnified image of semen and the moving image is transmitted from the smartphone to an external server, the external server performs a test based on the moving image and transmits the test result to the smartphone. In this technique, as a test result, for example, numerical values such as concentration and motility rate of sperm are calculated.

CITATION LIST

Patent Document

[Patent Document 1]
Japanese Patent No. 6045738

SUMMARY OF INVENTION

Technical Problem

However, it is difficult for a non-expert user to determine whether or not his sperm has an abnormality and to grasp the state of sperm, from the numerical values calculated by the technique described in Patent Document 1. Therefore, it is desired that the user can more easily grasp the state of sperm by providing not only the result shown by the numerical value but also the expert's findings on the numerical value.

An object of the present disclosure is to provide a reporting device, a reporting method, a reporting program, and a reporting system that enable a user to more easily grasp the state of sperm.

Solution to Problem

In order to achieve the aforementioned objects, a reporting device according to one aspect of the present disclosure includes: a moving image receiving unit configured to receive a moving image obtained by imaging sperm of a user from a user terminal; a moving image processing unit configured to display the moving image received by the moving image receiving unit on an embryologist terminal; a report information receiving unit configured to receive, from the embryologist terminal, report information indicating a result obtained by analyzing the sperm of the user by an embryologist, based on the moving image displayed on the embryologist terminal; and a report information processing unit configured to display the report information received by the report information receiving unit on the user terminal.

A reporting method according to one aspect of the present disclosure includes: receiving, by a moving image receiving unit, a moving image obtained by imaging sperm of a user from a user terminal; displaying, by a moving image processing unit, the moving image received by the moving image receiving unit on an embryologist terminal; receiving, by a report information receiving unit, from the embryologist terminal, report information indicating a result obtained by analyzing the sperm of the user by an embryologist, based on the moving image displayed on the embryologist terminal; and displaying, by a report information processing unit, the report information received by the report information receiving unit on the user terminal.

A reporting program according to one aspect of the present disclosure causes a computer to function as: a moving image receiving unit configured to receive a moving image obtained by imaging sperm of a user from a user terminal; a moving image processing unit configured to display the moving image received by the moving image receiving unit on an embryologist terminal; a report information receiving unit configured to receive, from the embryologist terminal, report information indicating a result obtained by analyzing the sperm of the user by an embryologist, based on the moving image displayed on the embryologist terminal; and a report information processing unit configured to display the report information received by the report information receiving unit on the user terminal.

A reporting system according to one aspect of the present disclosure includes a reporting device, a user terminal, and an embryologist terminal, in which the reporting device includes a moving image receiving unit configured to receive a moving image obtained by imaging sperm of a user from a user terminal; a moving image processing unit configured to display the moving image received by the moving image receiving unit on an embryologist terminal; a report information receiving unit configured to receive, from the embryologist terminal, report information indicating a result obtained by analyzing the sperm of the user by an embryologist, based on the moving image displayed on the embryologist terminal; and a report information processing unit configured to display the report information received by the report information receiving unit on the user terminal, the user terminal includes a moving image acquisition unit configured to acquire the moving image; a moving image transmission unit configured to transmit the moving image acquired by the moving image acquisition unit to the reporting device; and a first display unit configured to display the report information, and the embryologist terminal includes a second display unit configured to display the moving image; a report information acquisition unit configured to acquire the report information input by the embryologist, based on the moving image displayed on the second display unit; and a report information transmission unit configured to transmit the report information acquired by the report information acquisition unit to the reporting 100 device.

Advantageous Effects of Invention

According to the present disclosure, the user can more easily grasp the state of sperm.

BRIEF DESCRIPTION OF DRAWINGS

FIG. 3 is a diagram representing an example of a report.

DESCRIPTION OF EMBODIMENTS

The present disclosure relates to a reporting system in which an embryologist analyzes a state of sperm of a user and provides the user with a report showing the results of the analysis. The embryologist is a medical worker who is in charge of assisted reproductive technology such as in vitro fertilization in the field of infertility treatment. The embryologist is also an expert in the quantitative and qualitative analysis of sperm. In the reporting system of the present embodiment, the user uploads a moving image obtained by capturing the appearance of his sperm to the system. The embryologist analyzes the state of the user s sperm based on the moving image uploaded by the user. The embryologist creates the report information to be displayed in the report, based on the analysis result, and uploads the created report information to the system. Then, the user can grasp the state of his sperm by checking the report output based on the report information uploaded to the system.

Hereinafter, an embodiment of the present disclosure will be described in detail with reference to the drawings.

Figure 1:
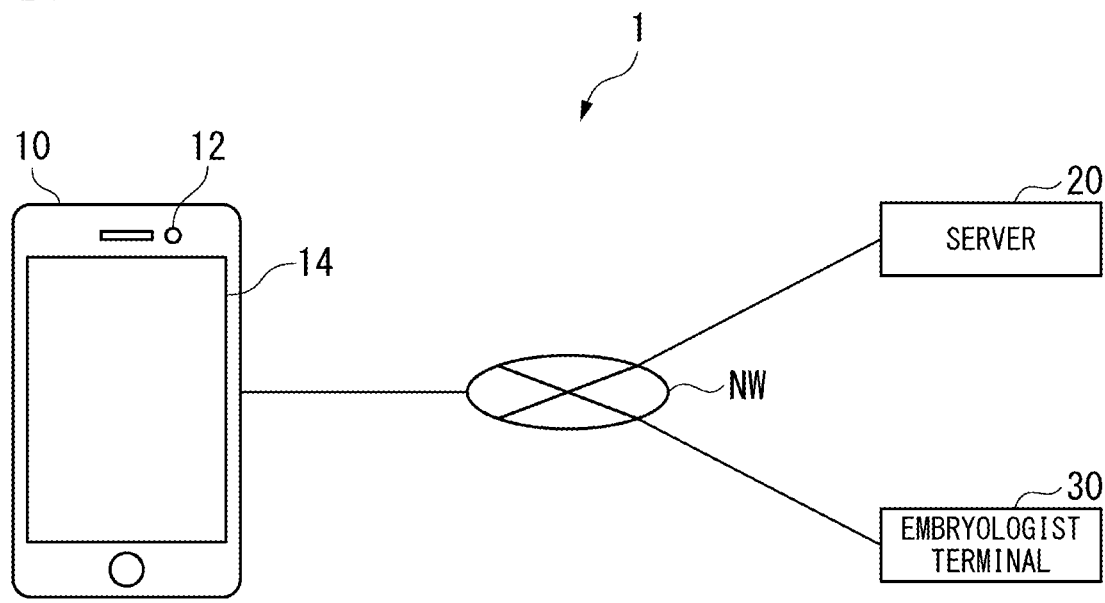
FIG. 1 is a diagram representing an example of a configuration of a reporting system.

FIG. 1 is a diagram representing an example of a configuration of a reporting system according to an embodiment of the present disclosure. The reporting system 1 of the present embodiment includes a user terminal 10, a server 20, and an embryologist terminal 30 shown in FIG. 1.

The user terminal 10 is a terminal operated by the user. The user terminal 10 is implemented by, for example, a smartphone. The user terminal 10 is communicably connected to the server 20, via the network NW. The terminal that implements the user terminal 10 is not limited to a smartphone as long as it is a terminal provided with a camera capable of capturing a sperm moving image. For example, the user terminal 10 may be implemented by a terminal such as a tablet terminal or a Personal Computer (PC). The camera may be built in each terminal or may be externally connected to each terminal. The Operating System (OS) mounted on the user terminal 10 may be any one of, for example, Android (registered trademark), iOS (registered trademark), Windows (registered trademark), and MacOS (registered trademark), depending on the type of the user terminal 10. The type of OS is not limited to this example.

The user operates the user terminal 10 to capture a moving image of the user's sperm. For example, the user captures a sperm moving image by using a kit for having an embryologist analyze the state of his sperm and the front camera 12 of the user terminal 10.

The kit includes, for example, an observation loupe, a serial code for report application, a graduated measuring tube, a collection cup, a collection stick, and a double-sided sticker. The observation loupe is for magnifying and imaging the user's sperm. The serial code for report application is information for identifying a user (an example of user identification information). The graduated measuring tube is for measuring the amount of semen of the user. The collection cup is a container that holds the semen collected by the user. The collection stick is for attaching the semen collected by the user to the observation loupe. The double-sided sticker is for fixing the observation loupe to the front camera 12 of the user terminal 10.

Figure 2:
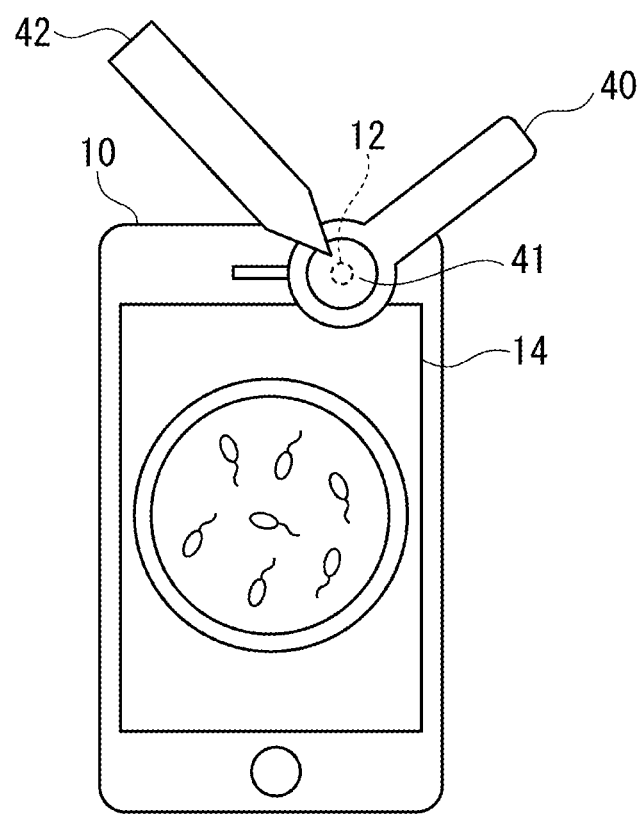
FIG. 2 is a diagram representing an example of a method for capturing a sperm moving image.

Here, with reference to FIG. 2, an example of a method for capturing a sperm moving image according to the embodiment of the present disclosure will be described. FIG. 2 is a diagram representing an example of a method for capturing the sperm moving image according to the embodiment of the present disclosure. FIG. 2 shows a method for capturing a sperm moving image by using a kit.

First, the user collects semen in the collection cup. After collection, the user leaves the collected semen for about 10 to 20 minutes until the collected semen liquefies. The user uses the double-sided sticker to fix the observation loupe 40 on the front camera 12 of the user terminal 10 as shown in FIG. 2. When the collected semen is liquefied, the collected semen is attached to the lens 41 of the observation loupe 40 by using the collection stick 42. When the front camera 12 is started in this state, the front camera 12 can image the sperm magnified by the observation loupe. Further, the appearance of sperm imaged by the front camera 12 is displayed on the touch screen 14 of the user terminal 10. This allows the user to observe the appearance of his sperm. Further, the user can capture the sperm moving image by operating the user terminal 10 to start capturing of the sperm moving image.

The user uploads (registers) the captured sperm moving image to the server 20. For example, the user uploads the captured sperm moving image to the server 20, via the Web application. Specifically, the user starts the Web browser on the user terminal 10 and accesses the Web application by designating the Uniform Resource Locator (URL) of the Web application. Then, the user logs in to the Web application by using the login information registered in advance. After logging in, the user inputs an operation for uploading the sperm moving image to the server 20. When the user inputs the upload operation of the sperm moving image, the user terminal 10 transmits the sperm moving image to the server 20, via the network NW.

In the present embodiment, the user can upload a plurality of moving images (for example, up to three) to one serial code. When a plurality of moving images are uploaded, the embryologist creates report information including the analysis results for each moving image and the comprehensive analysis results for the plurality of moving images. When the user uploads only one moving image and the moving image happens to be a moving image of sperm in poor state, the embryologist has no choice but to create report information showing a bad result. As a result, the user obtains a report showing the bad result. On the other hand, when the user uploads a plurality of moving images, the embryologist can create report information that is comprehensively determined by comparing each moving image. For example, when the user uploads two or three moving images with different collection dates, even if one of the moving images happens to be a moving image of sperm in poor state, if the sperm states of the other moving images are good, the user may obtain a report showing overall good results. That is, if a plurality of moving images are uploaded, the number of samples to be analyzed increases, so that the user can obtain a report showing the state of his sperm more accurately.

In addition, the user causes the user terminal 10 to display the report. For example, the user causes the user terminal 10 to display the report, via the Web application. Specifically, the user logs in to the Web application and inputs an operation for displaying the report. When a report display operation is input from the user, the user terminal 10 transmits a request to output the report to the server 20, via the network NW. The server 20 that has received the request outputs the report and displays the report on the embryologist terminal 30 via the Web application.

In the report, for example, parameter information indicating the state of the user s sperm and the findings of the embryologist based on the parameter information are displayed as report information. The parameter information specifically includes information such as a semen amount, a sperm concentration, a sperm motility rate, a total sperm count, and a total motile sperm count. The embryologist's findings specifically include information such as overall findings based on a plurality of moving images and findings based on World Health Organization (WHO) reference values.

Here, an example of a report according to the embodiment of the present disclosure will be described with reference to FIG. 3. FIG. 3 is a diagram representing an example of a report according to the embodiment of the present disclosure. FIG. 3 shows an example of a report when two moving images are uploaded by the user.

As shown in FIG. 3, the upload date and serial code of the report are displayed in an area A1 of the report 50. Parameter information related to each moving image is displayed in an area A2. Parameter information related to a first moving image is displayed in an area A2-1. Parameter information related to a second moving image is displayed in an area A2-2. The overall findings are displayed in an area A3. Findings based on the WHO reference values are displayed in an area A4.

The server 20 is a device that manages reporting. The server 20 according to the present embodiment is an example of a reporting device. The server 20 is implemented by, for example, a PC. The server 20 is communicably connected to the user terminal 10 and the embryologist terminal 30, via the network NW. For example, the server 20 receives a sperm moving image transmitted from the user terminal 10, via the network NW. The server 20 stores the received sperm moving image in association with the user's identification information. After the storage, the server 20 reproduces the stored sperm moving image and displays the reproduced moving image on the embryologist terminal 30, in response to the request received from the embryologist terminal 30 via the network NW. Further, the server 20 receives the report information transmitted from the embryologist terminal 30, via the network NW. The server 20 stores the received report information in association with the user's identification information. After storage, the server 20 displays the stored report information as a report on the user terminal 10, in response to a request received from the user terminal 10 via the network NW.

The embryologist terminal 30 is a terminal operated by the embryologist. The embryologist terminal 30 is implemented by, for example, a PC. The embryologist terminal 30 is communicably connected to the server 20, via the network NW. The terminal that implements the embryologist terminal 30 is not limited to the PC. For example, the embryologist terminal 30 may be implemented by a terminal such as a smartphone or a tablet terminal.

The embryologist operates the embryologist terminal 30 to display a moving image of the user's sperm on the embryologist terminal 30. For example, the embryologist causes the server 20 to reproduce the sperm moving image, via the Web application and display the reproduced moving image on the embryologist terminal 30. Specifically, the embryologist starts the Web browser on the embryologist terminal 30 and accesses the Web application by designating the URL of the Web application. Then, the embryologist logs in to the Web application by using the login information registered in advance. After logging in, the embryologist inputs an operation for displaying the moving image to be analyzed on the embryologist terminal 30. When a sperm moving image display operation is input from the embryologist, the embryologist terminal 30 transmits a request to reproduce the moving image to be analyzed to the server 20, via the network NW. The server 20 that has received the request reproduces the moving image to be analyzed, and displays the moving image being reproduced on the embryologist terminal 30 via the Web application. The embryologist analyzes the state of the user's sperm based on the moving image displayed on the embryologist terminal 30.

After the analysis, the embryologist uploads the report information showing the analysis result to the server 20. For example, the embryologist uploads the report information to the server 20, via the Web application. Specifically, the embryologist logs in to the Web application, and inputs an operation for uploading the report information to the server 20. When the report information upload operation is input from the embryologist, the embryologist terminal 30 transmits the report information to the server 20, via the network NW.

As described above, when the user captures a moving image of his sperm by using the user terminal 10 such as a smartphone and a kit, and uploads the moving image to the server 20 via a network, the user can receive sperm analysis while at home. Thus, the user can save the time and effort of submitting sperm to the medical institution by going to the hospital or mail. Further, the cost of the kit may be lower than the cost of going to the hospital. In this case, the user can receive the sperm analysis using the kit, which can reduce the cost as compared with the case where the sperm is analyzed by going to the hospital. From the above, the user can reduce the time and effort required for sperm analysis by using the kit, and in some cases, the cost can be reduced, so that the user can easily receive sperm analysis. Therefore, it can lead to an early consultation for sperm analysis.

Further, the reporting system of the present embodiment allows the user to receive report information showing the analysis result by an expert such as an embryologist as a report. For example, only the data calculated as a numerical value is described in the report information mechanically created by the server or the like, so that it is difficult for the user to grasp the state of his sperm from the data. The report information created by the expert may include the expert's impression of the data. Therefore, by receiving the report information created by an expert such as an embryologist, the user can easily grasp the state of his sperm by referring to the impression of the expert.

In the case of a system in which report information is mechanically created by the server as in the past, when a moving image that is out of focus on sperm is uploaded, the server cannot analyze the moving image due to the out-of-focus and an error is output in many cases. If an error is output in the case of a system where only one moving image can be uploaded at once, the user cannot upload the moving image again, so that the report cannot be received and the cost is wasted. On the other hand, in the reporting system of the present embodiment, the moving image is analyzed by an embryologist (person). Even if the uploaded sperm moving image is out of focus, the embryologist can analyze the moving image by considering ambiguity due to the out-of-focus to some extent. Therefore, in the reporting system of the present embodiment, even if the uploaded moving image is out of focus, the user can receive a report in which ambiguity due to the out-of-focus is considered to some extent. Therefore, the reporting system of the present embodiment can reduce the frequency with which the user cannot receive the report due to the out-of-focus of the moving image and the frequency with which the cost is wasted.

Figure 4:
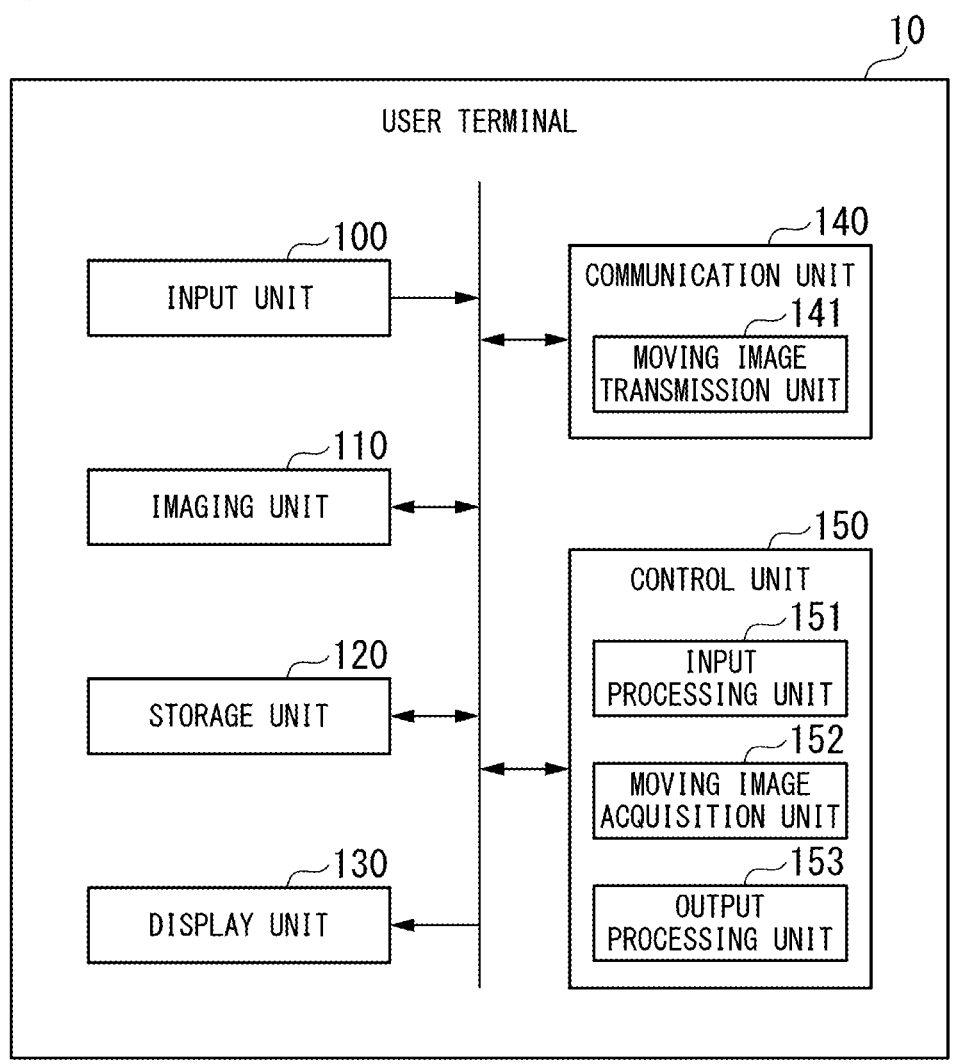
FIG. 4 is a block diagram representing an example of a functional configuration of a user terminal.

FIG. 4 is a block diagram representing an example of the functional configuration of the user terminal 10 according to the embodiment of the present disclosure. The user terminal 10 of the present embodiment includes an input unit 100, an imaging unit 110, a storage unit 120, a display unit 130 (first display unit), a communication unit 140, and a control unit 150.

The input unit 100 has a function of receiving an operation input by the user. The function of the input unit 100 is implemented by, for example, a touch screen 14 that the user terminal 10 has as hardware. The function of the input unit 100 may be implemented by an input device such as a keyboard or a mouse. The input unit 100 receives inputs such as an operation of capturing a sperm moving image, the upload operation of the sperm moving image, and a report display operation. The input unit 100 outputs the received input to the control unit 150.

The imaging unit 110 has a function of capturing a moving image of user's sperm. The function of the imaging unit 110 is implemented by, for example, a camera (for example, a front camera 12) that the user terminal 10 has as hardware, a camera externally connected to the user terminal 10, or the like. The imaging unit 110 outputs the captured sperm moving image to the control unit 150.

The storage unit 120 has a function of storing various types of information. The storage unit 120 is composed of a storage medium, for example, a Hard Disk Drive (HDD), a flash memory, an Electrically Erasable Programmable Read Only Memory (EEPROM), a Random Access read/write Memory (RAM), a Read Only Memory (ROM), or any combination of these storage media. For the storage unit 120, for example, a non-volatile memory can be used. For example, the storage unit 120 stores the moving image of the user's sperm captured by the imaging unit 110.

The display unit 130 has a function of displaying a sperm moving image or a report. The function of the display unit 130 is implemented by, for example, a touch screen that the user terminal 10 has as hardware. The display unit 130 displays, for example, a sperm moving image captured by the imaging unit 110, or display a report including report information stored in the server 20, based on the control by the control unit 150.

The communication unit 140 has a function of transmitting and receiving various types of information. The function of the communication unit 140 is implemented by, for example, a communication device that the user terminal 10 has as hardware. As shown in FIG. 4, the communication unit 140 includes a moving image transmission unit 141. The moving image transmission unit 141 has a function of transmitting a sperm moving image to the server 20, via the network NW. For example, the moving image transmission unit 141 transmits the sperm moving image captured by the imaging unit 110 to the server 20, based on the control by the control unit 150.

The moving image transmission unit 141 transmits at least one moving image to the server 20. That is, the moving image transmission unit 141 may transmit a moving image of a plurality of sperms to the server 20. In the present embodiment, the moving image transmission unit 141 transmits up to three moving images to the server 20 with respect to one piece of identification information of the user.

The control unit 150 has a function of controlling the overall operation of the user terminal 10. The function of the control unit 150 is implemented, for example, by causing a Central Processing Unit (CPU) that the user terminal 10 has as hardware to execute a program.

As shown in FIG. 4, the control unit 150 includes an input processing unit 151, a moving image acquisition unit 152, and an output processing unit 153.

The input processing unit 151 performs control, based on the input received by the input unit 100. For example, when the input unit 100 receives an operation of capturing a sperm moving image, the input processing unit 151 causes the moving image acquisition unit 152 to perform a sperm moving image acquisition process. Further, when the input unit 100 receives the upload operation of the sperm moving image, the input processing unit 151 causes the moving image transmission unit 141 to perform the transmission process. When the input unit 100 receives the report display operation, the input processing unit 151 causes the output processing unit 153 to perform an output process. For example, the input processing unit 151 causes the output processing unit 153 to perform the output process of a report, based on the operation.

The moving image acquisition unit 152 has a function of acquiring a sperm moving image, based on the control of the input processing unit 151. For example, when the moving image acquisition unit 152 receives an instruction from the input processing unit 151, the imaging unit 110 is made to capture a sperm moving image, and the sperm moving image captured by the imaging unit 110 is acquired. The acquisition destination of the sperm moving image is not limited to the imaging unit 110. For example, the moving image acquisition unit 152 may acquire a sperm moving image captured by an external terminal, via the communication unit 140. The moving image acquisition unit 152 transmits the acquired sperm moving image from the moving image transmission unit 141 to the server 20. The moving image acquisition unit 152 may store the acquired sperm moving image in the storage unit 120.

The output processing unit 153 has a function of displaying a report on the display unit 130, based on the control of the input processing unit 151. For example, when receiving an instruction from the input processing unit 151, the output processing unit 153 displays the report output by the server 20 on the display unit 130, via the Web application.

Figure 5:
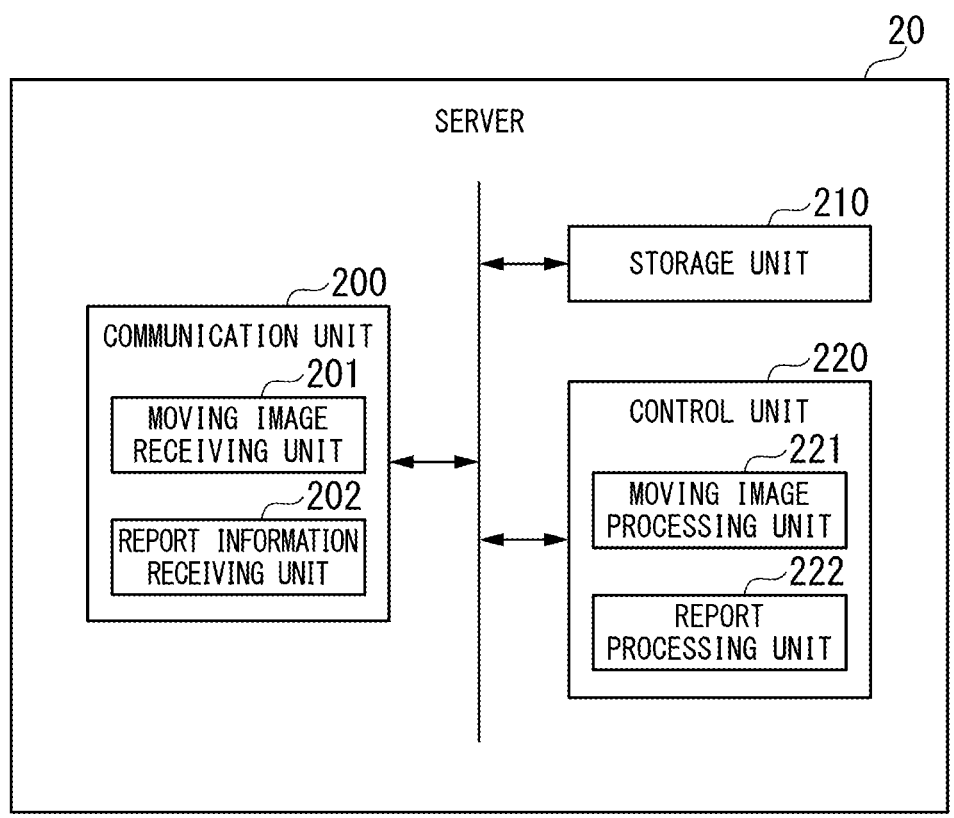
FIG. 5 is a block diagram representing an example of a functional configuration of a server.

FIG. 5 is a block diagram representing an example of the functional configuration of the server 20 according to the embodiment of the present disclosure. The server 20 includes a communication unit 200, a storage unit 210, and a control unit 220.

The communication unit 200 has a function of transmitting and receiving various types of information. The function of the communication unit 200 is implemented by, for example, a communication device that the server 20 has as hardware.

As shown in FIG. 5, the communication unit 200 includes a moving image receiving unit 201 and a report information receiving unit 202.

The moving image receiving unit 201 has a function of receiving a sperm moving image from the user terminal 10, via the network NW. The moving image receiving unit 201 associates the sperm moving image received from the user terminal 10 with the user's identification information (for example, a serial code) and stores the associated image in the storage unit 210.

The moving image receiving unit 201 receives at least one sperm moving image from the user terminal 10 with respect to one piece of identification information of the user. That is, the moving image receiving unit 201 may receive a plurality of sperm moving images from the user terminal 10 with respect to one piece of identification information of the user. In the present embodiment, the moving image receiving unit 201 receives up to three moving images from the user terminal 10 with respect to one piece of identification information of the user. When receiving a plurality of sperm moving images, the moving image receiving unit 201 stores each moving image in the storage unit 210 in association with the identification information of the same user.

The user identification information is transmitted from the user terminal 10 together with the sperm moving image.

The report information receiving unit 202 has a function of receiving report information from the embryologist terminal 30, via the network NW. The report information receiving unit 202 stores the report information received from the embryologist terminal 30 in the storage unit 210 in association with the user's identification information.

The report information receiving unit 202 receives the report information including the analysis result according to the number of moving images displayed on the embryologist terminal 30 from the embryologist terminal 30. When only one moving image is displayed on the embryologist terminal 30, the report information receiving unit 202 receives the report information including the parameter information and the findings for one moving image. When a plurality of moving images are displayed on the embryologist terminal 30, the report information receiving unit 202 receives the report information including the parameter information for each moving image and the findings of the embryologist for the plurality of moving images.

The storage unit 210 has a function of storing various types of information. The storage unit 210 is composed of a storage medium, for example, an HDD, a flash memory, an EEPROM, a RAM, a ROM, or any combination of these storage media. For the storage unit 210, for example, a non-volatile memory can be used. The storage unit 210 stores, for example, a sperm moving image and report information in association with user identification information.

The control unit 220 has a function of controlling the overall operation of the server 20. The function of the control unit 220 is implemented, for example, by causing a CPU that the server 20 has as hardware to execute a program. As shown in FIG. 5, the control unit 220 includes a moving image processing unit 221 and a report processing unit 222.

The moving image processing unit 221 has a function of controlling a process of displaying a sperm moving image on the embryologist terminal 30. For example, when the communication unit 200 receives a request for a sperm moving image from the embryologist terminal 30, the moving image processing unit 221 reproduces the target sperm moving image stored in the storage unit 210. Then, the moving image processing unit 221 displays the sperm moving image being reproduced on the embryologist terminal 30, via the Web application.

The report processing unit 222 has a function of controlling a process of displaying a report on the user terminal 10. For example, when the communication unit 200 receives a report request from the user terminal 10, the report processing unit 222 displays a report including the target report information stored in the storage unit 210 on the user terminal 10, via the Web application. As an example, the report processing unit 222 displays a report having the layout shown in FIG. 3, on the user terminal 10.

When the report information received by the report information receiving unit 202 from the embryologist terminal 30 is stored (registered) in the storage unit 210, the report processing unit 222 transmits an email notifying that the report has been registered, from the communication unit 200 to the user terminal 10 (user's email address).

Figure 6:
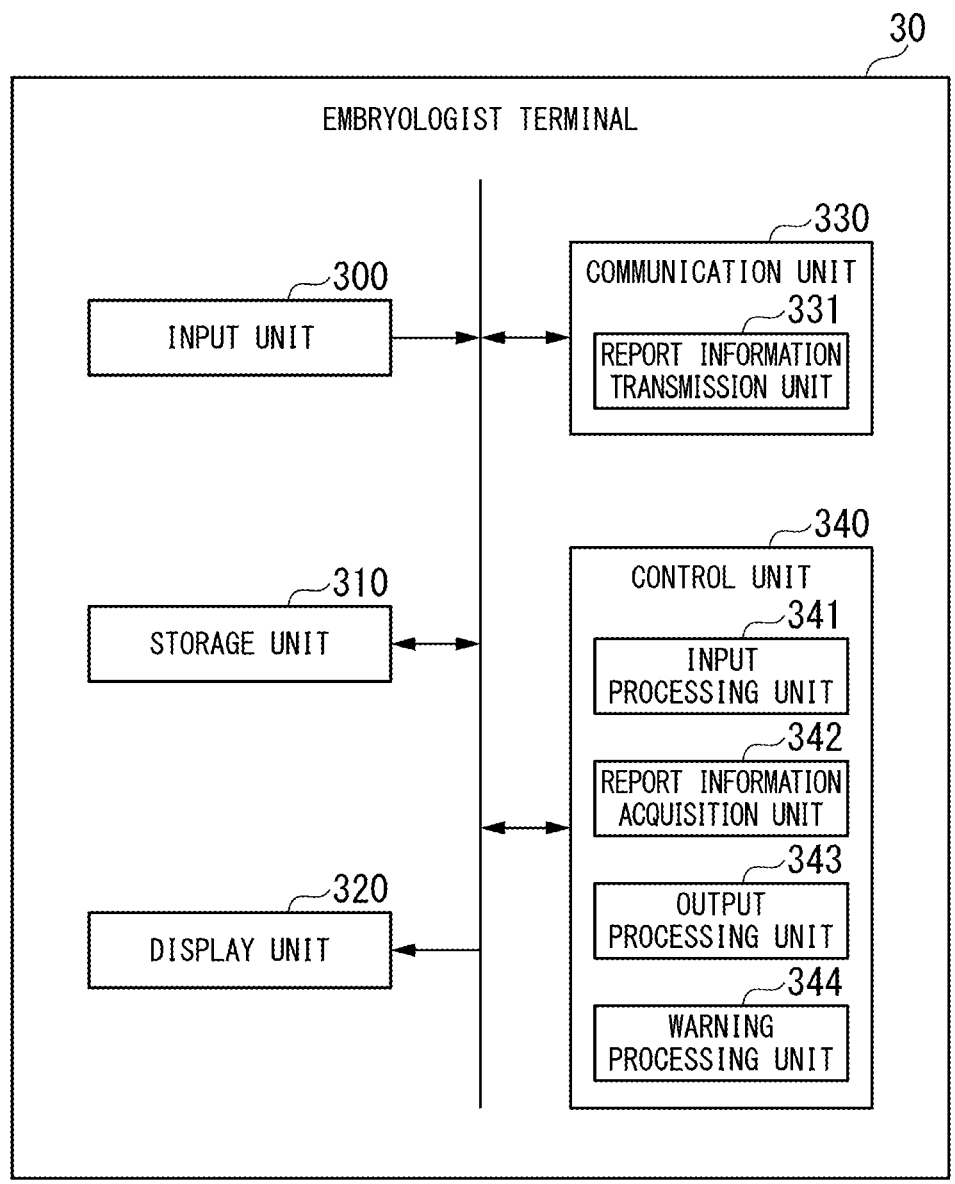
FIG. 6 is a block diagram representing an example of a functional configuration of an embryologist terminal.

FIG. 6 is a block diagram representing an example of the functional configuration of the embryologist terminal 30 according to the embodiment of the present disclosure. The embryologist terminal 30 of the present embodiment includes an input unit 300, a storage unit 310, a display unit 320 (second display unit), a communication unit 330, and a control unit 340.

The input unit 300 has a function of receiving an input of an operation by an embryologist. The function of the input unit 300 is implemented by, for example, an input device such as a keyboard or a mouse that the embryologist terminal 30 has as hardware. The input unit 300 receives inputs such as a sperm moving image display operation, a report information input operation, and a report information upload operation. The input unit 300 outputs the received input to the control unit 340.

The storage unit 310 has a function of storing various types of information. The storage unit 310 is composed of a storage medium, for example, an HDD, a flash memory, an EEPROM, a RAM, a ROM, or any combination of these storage media. For the storage unit 310, for example, a non-volatile memory can be used.

The display unit 320 has a function of displaying a sperm moving image. The function of the display unit 320 is implemented by, for example, a display device such as a display that the embryologist terminal 30 has as hardware. The display unit 320 displays, for example, a sperm moving image reproduced by the server 20, based on control by the control unit 340. The embryologist can analyze the user's sperm by watching the sperm moving image displayed on the display unit 320.

The communication unit 330 has a function of transmitting and receiving various types of information. The function of the communication unit 330 is implemented by, for example, a communication device that the embryologist terminal 30 has as hardware.

As shown in FIG. 6, the communication unit 330 includes a report information transmission unit 331.

The report information transmission unit 331 transmits the report information to the server 20, via the network NW. For example, the report information transmission unit 331 transmits the report information input by the embryologist to the server 20, based on the control by the control unit 340.

The control unit 340 has a function of controlling the overall operation of the embryologist terminal 30. The function of the control unit 340 is implemented, for example, by causing a CPU that the embryologist terminal 30 has as hardware to execute a program.

As shown in FIG. 6, the control unit 340 includes an input processing unit 341, a report information acquisition unit 342, an output processing unit 343, and a warning processing unit 344.

The input processing unit 341 performs control, based on the input received by the input unit 300. For example, when the input unit 300 receives a sperm moving image display operation, the input processing unit 341 causes the output processing unit 343 to perform an output process. When the input unit 300 receives the report information input operation, the input processing unit 341 causes the report information acquisition unit 342 to perform the report information acquisition process. When the input unit 300 receives the report information upload operation, the input processing unit 341 causes the report information transmission unit 331 to perform the transmission process.

The report information acquisition unit 342 has a function of acquiring report information, based on the control of the input processing unit 341. For example, when receiving an instruction from the input processing unit 341, the report information acquisition unit 342 acquires the report information to be input based on the moving image displayed on the display unit 320 by the embryologist. The report information acquisition unit 342 transmits the acquired report information from the report information transmission unit 331 to the server 20.

The output processing unit 343 has a function of displaying a sperm moving image on the display unit 320, based on the control of the input processing unit 341. For example, when receiving an instruction from the input processing unit 341, the output processing unit 343 displays the sperm moving image being reproduced by the server 20 on the display unit 320, via the Web application.

The warning processing unit 344 has a function of notifying a warning. For example, in a case where a predetermined period has elapsed (for example, three days or more have elapsed) while the status of the sperm moving image registered as an unsupported case is "unsupported", the warning processing unit 344 transmits an email indicating a warning that the unsupported state continues, a warning to urge the implementation of analysis from the communication unit 330, or the like to the email address of the embryologist. The warning processing unit 344 may display the warning on the display unit 320. In addition, "unsupported" means that the person in charge of analysis does not make a determination.

Further, when the user uploads the sperm moving image to the server 20 and the embryologist cannot complete the analysis of the sperm moving image within a predetermined period (for example, within five days), the warning processing unit 344 transmits an email indicating a warning from the communication unit 330 to the email address of the embryologist.

Figure 7:
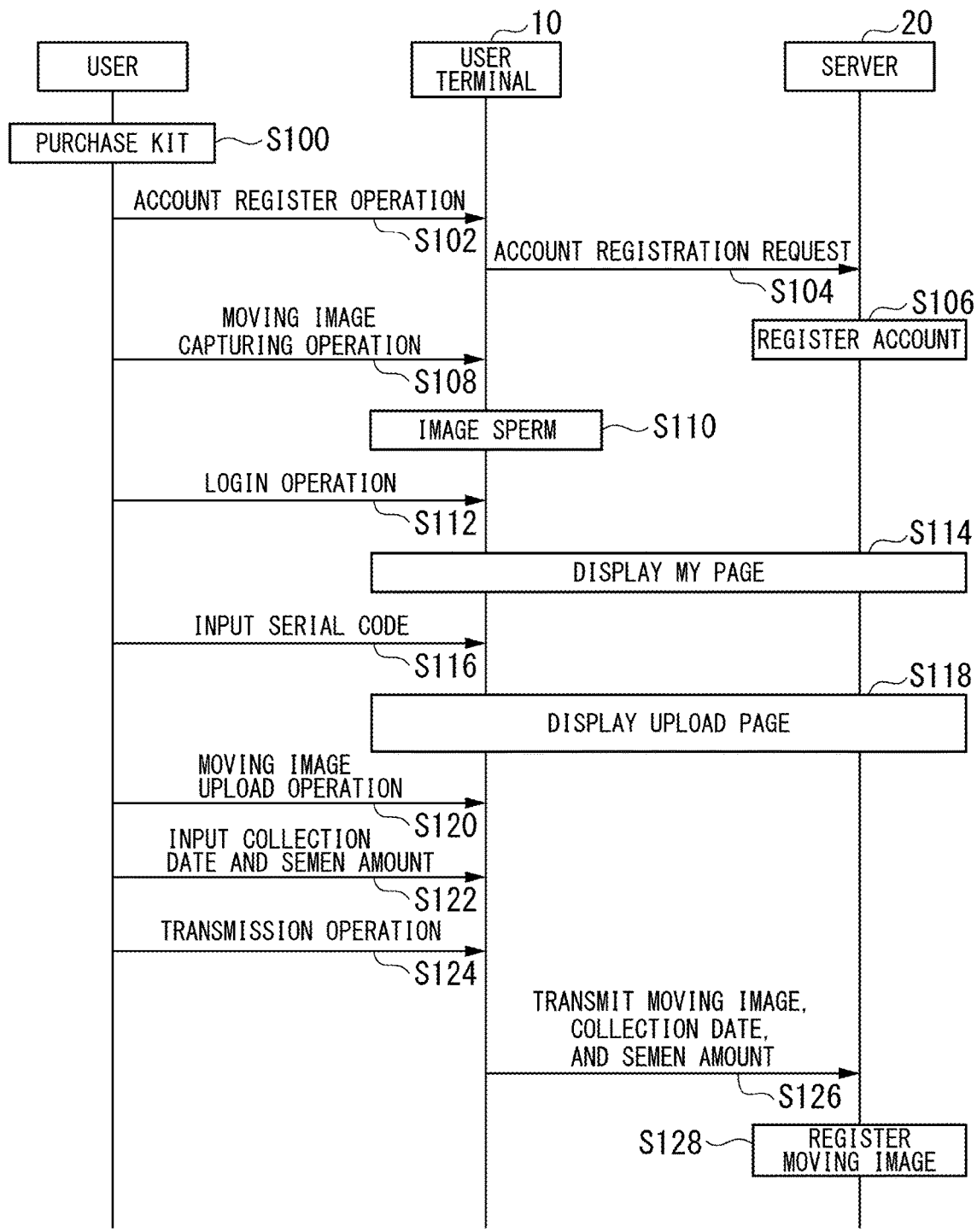
FIG. 7 is a sequence diagram representing an example of a processing flow until a sperm moving image is registered in the server.

FIG. 7 is a sequence diagram representing an example of a processing flow until the sperm moving image is registered in the server 20, according to the embodiment of the present disclosure.

As shown in FIG. 7, the user first purchases the kit (S100). The user inputs an operation for registering an account, to the user terminal 10 (S102). Specifically, the user accesses the URL of the sign-up page described in the accessory of the kit, and inputs an email address and any password. After inputting, when the user clicks the URL for the confirmation email, the confirmation email is transmitted. When the operation for registering the account by the user is completed, the user terminal 10 transmits an account registration request to the server 20 (S104). The server 20 that has received the account registration request registers the user's account (S106).

Subsequently, the user inputs an operation for capturing a sperm moving image to the user terminal 10 (S108). The user terminal 10, to which the operation for capturing a sperm moving image is input, captures the sperm moving image (S110). Specifically, the user captures a sperm moving image, by the method described with reference to FIG. 2.

After capturing the sperm moving image, the user inputs an operation for logging in to the Web application to the user terminal 10 (S112). The user terminal 10, to which the operation for logging in is input, displays My Page (S114). In S114, first, the user terminal 10 transmits the login information to the server 20. Next, the server 20 performs authentication, based on the received login information. After successful authentication, the server 20 transmits My Page information to the user terminal 10. The user terminal 10 displays My Page, based on the received My Page information.

The user inputs the serial code for report application described in the accessories of the kit, on My Page (S116). The user terminal 10, to which the serial code is input, displays the upload page (S118). In S118, first, the user terminal 10 transmits the serial code to the server 20. Next, the server 20 determines whether or not the received serial code is correct. When the serial code is correct, the server 20 transmits the upload page information to the user terminal 10. The user terminal 10 displays the upload page, based on the received upload page information. When the serial code is incorrect, the user terminal 10 displays an error message.

After displaying the upload page, the user inputs an upload operation of the sperm moving image (S120). Further, the user inputs a semen collection date and a semen amount to the user terminal 10 (S122). After the input, when the user inputs a transmission operation (S124), the sperm moving image, the collection date, and the semen amount are transmitted from the user terminal 10 to the server 20 (S126). The server 20 registers the sperm moving image received from the user terminal 10 (S128). The server 20 also registers the received collection date and the semen amount.

Figure 8:
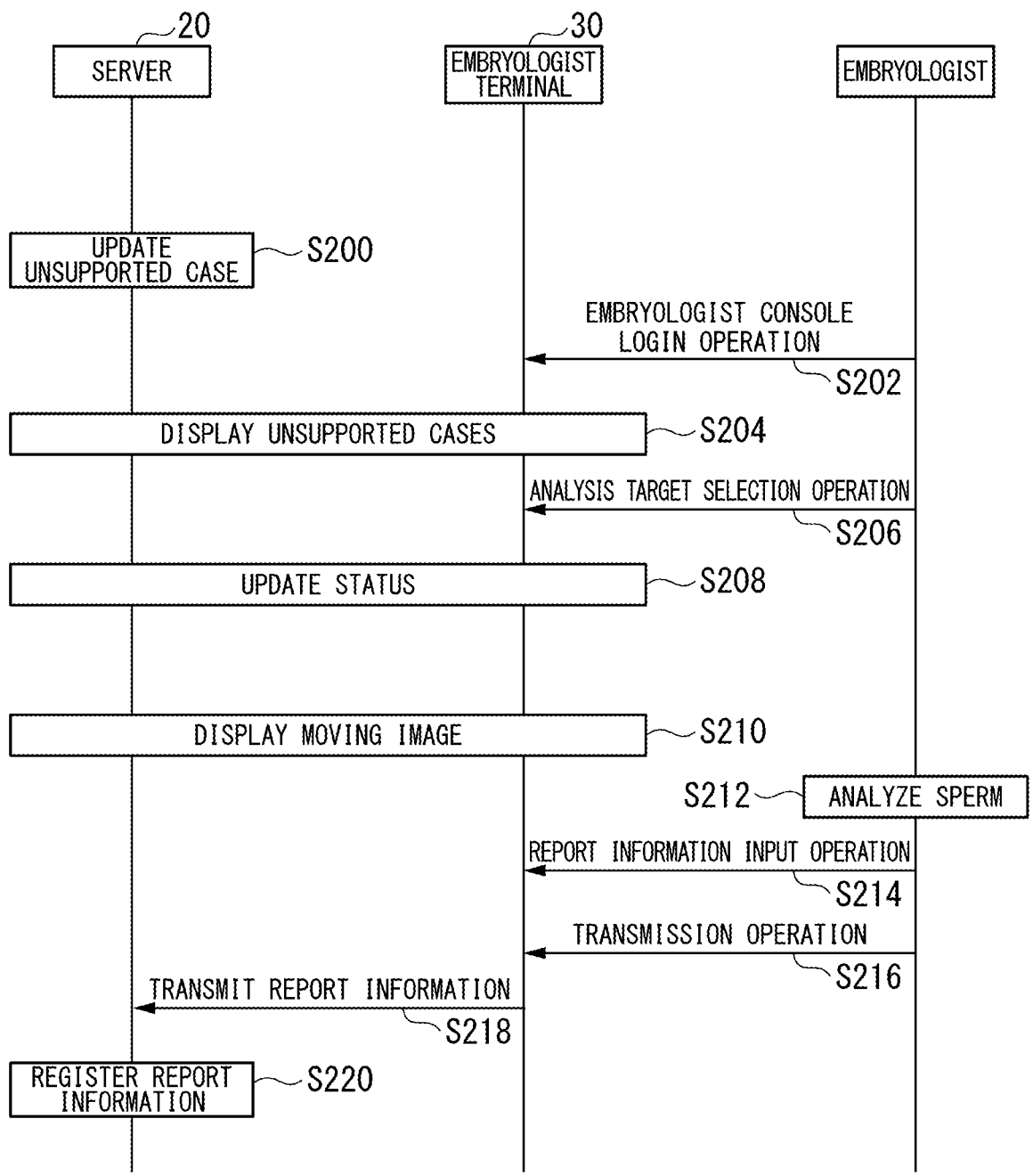
FIG. 8 is a sequence diagram representing an example of a processing flow until report information is registered in the server since the sperm moving image is registered.

FIG. 8 is a sequence diagram representing an example of a processing flow until report information is registered in the server 20 since the sperm moving image is registered, according to the embodiment of the present disclosure. FIG. 8 shows a continuation of the sequence diagram shown in FIG. 7.

As shown in FIG. 8, first, when the sperm moving image is registered, the server 20 updates the unsupported case that the embryologist has not performed the analysis (S200).

The embryologist inputs an operation for logging in to the embryologist console (Web application) to the embryologist terminal 30 (S202). The embryologist terminal 30 displays a list of unsupported cases (S204). In S204, first, the embryologist terminal 30 transmits the login information to the server 20. Next, the server 20 transmits the unsupported case information corresponding to the login information to the embryologist terminal 30, based on the received login information. The embryologist terminal 30 displays a list of unsupported cases, based on the received unsupported case information. The embryologist inputs an operation for selecting an analysis target from the list of unsupported cases to the embryologist terminal 30 (S206).

The embryologist terminal 30 updates the status of the analysis target selected by the embryologist (S208). In S208, first, the embryologist terminal 30 transmits the moving image information selected by the embryologist to the server 20. Next, the server 20 updates the status, based on the received moving image information. For example, the server 20 updates the status from "unsupported" to "being supported". After the update, the server 20 transmits the updated status information to the embryologist terminal 30. The embryologist terminal 30 updates the status display, based on the received status information. The embryologist terminal 30 displays a sperm moving image selected by the embryologist (S210). In S210, first, the embryologist terminal 30 transmits a reproduction request of the sperm moving image selected by the embryologist to the server 20. The server 20 then reproduces the sperm moving image corresponding to the received request. Next, the embryologist terminal 30 displays a sperm moving image being reproduced by the server 20, via the Web application.

The embryologist analyzes the sperm, based on the sperm moving image displayed on the embryologist terminal 30 (S212). After the analysis, the embryologist performs the report information input operation to the embryologist terminal 30 (S214). After inputting the report information, when the embryologist inputs the transmission operation (S216), the report information is transmitted from the embryologist terminal 30 to the server 20 (S218). The server 20 registers the report information received from the embryologist terminal 30 (S220).

Figure 9:
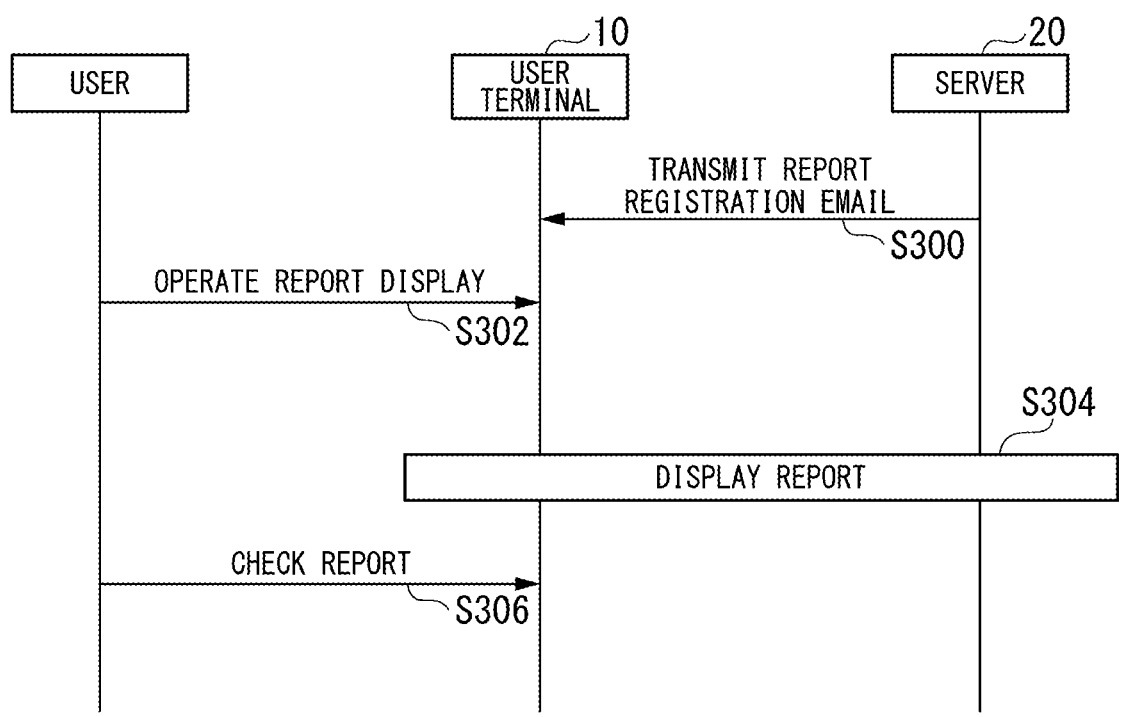
FIG. 9 is a sequence diagram representing an example of a processing flow until a report is displayed on the user terminal since the report information is registered.

FIG. 9 is a sequence diagram representing an example of a processing flow from the registration of the report information to the display of the report information on the user terminal 10, according to the embodiment of the present disclosure. FIG. 9 shows a continuation of the sequence diagram shown in FIG. 8.

As shown in FIG. 9, first, the server 20 transmits a report registration email to the user terminal 10 (S300). The user who has checked the report registration email inputs an operation for displaying the report to the user terminal 10 (S302). The user terminal 10 displays a report (S304). In S304, first, the user terminal 10 transmits a display request for the report selected by the user to the server 20. Next, the server 20 outputs a report corresponding to the received request. Next, the user terminal 10 displays the report output by the server 20, via the Web application. The user checks the report displayed on the user terminal 10 (S306).

As described above, the reporting device (server 20) according to the present embodiment receives a moving image of the user's sperm from the user terminal 10. In addition, the reporting device displays the received moving image on the embryologist terminal 30. Further, the reporting device receives, from the embryologist terminal 30, report information indicating the state of the user's sperm, which the embryologist inputs to the embryologist terminal 30 based on the moving image displayed on the embryologist terminal 30. In addition, the reporting device displays the received report information on the user terminal.

With this configuration, the reporting device according to the present embodiment provides the embryologist with the moving image of the user's sperm, and provides the user with a report created by the embryologist analyzing the user's sperm based on the moving image. Thus, the user can check not only the analysis result including only the numerical value calculated mechanically but also the analysis result including also the findings of an expert. Therefore, by checking the findings of the expert, the user can easily grasp the state of his sperm, which is difficult to grasp only from the numerical value.

Therefore, the reporting device according to the present embodiment enables the user to more easily grasp the state of sperm.

The reporting device in the above-described embodiment may be implemented by a computer. In that case, a program for implementing this function may be recorded on a computer-readable recording medium, and the program recorded on the recording medium may be read and executed by a computer system to implement the reporting device. The term "computer system" as used herein includes an OS and hardware such as peripheral devices. Further, the "computer-readable recording medium" refers to a portable medium such as a flexible disk, a magneto-optical disk, a ROM, or a CD-ROM, or a storage device such as a hard disk built in a computer system. Further, a "computer-readable recording medium" may include those which dynamically hold programs for a short period of time, such as a communication line when a program is transmitted via a network such as the Internet or a communication line such as a telephone line, or those which hold programs for a certain period of time, such as a volatile memory inside a computer system that serves as a server or client in that case. Further, the above program may be for implementing a part of the above-described functions, may be for implementing the above-described functions in combination with a program already recorded in the computer system, or may be implemented by using a programmable logic device such as FPGA (Field Programmable Gate Array).

Although the embodiment of the present disclosure has been described in detail with reference to the drawings, the specific configuration is not limited to the above, and various design changes and the like can be made without departing from the gist of the present disclosure.

REFERENCE SIGNS LIST

1: Reporting system
10: User terminal
12: Front camera
14: Touch screen
20: Server
30: Embryologist terminal
40: Observation loupe
41: Lens
42: Collection stick
50: Report
100: Input unit 110: Imaging unit
120: Storage unit
130: Display unit
140: Communication unit
141: Moving image transmission unit
150: Control unit
151: Input processing unit
152: Moving image acquisition unit
153: Output processing unit
200: Communication unit
201: Moving image receiving unit
202: Report information receiving unit
210: Storage unit
220: Control unit
221: Moving image processing unit
222: Report processing unit
300: Input unit
310: Storage unit
320: Display unit
330: Communication unit
331: Report information transmission unit
340: Control unit
341: Input processing unit
342: Report information acquisition unit
343: Output processing unit
344: Warning processing unit

What is claimed is:

1. A reporting method comprising:
receiving from a user terminal, via a network, a moving image obtained by imaging sperm of a user, wherein the user terminal comprises a camera detachably attached to an observation loupe to magnify the moving image obtained by imaging the sperm of the user;
causing an embryologist terminal, via the network, to display the moving image received from the user terminal;
receiving, from the embryologist terminal, via the network, report information indicating a result obtained by analyzing the sperm of the user by an embryologist, based on the moving image displayed on the embryologist terminal;
causing the user terminal, via the network, to display the report information received from the embryologist terminal;
receiving, from the user terminal, via the network, a plurality of moving images with different collection dates of the sperm with respect to one piece of identification information of the user;
determining, for each of the plurality of moving images, a status based on whether analysis is performed on each of the plurality of moving images;
causing the embryologist terminal, via the network, to display the status for each of the plurality of moving images;
updating, for at least one of the plurality of moving images, the status from "unsupported" to "being supported," based on selection of the at least one of the plurality of moving images by the embryologist, and
causing the user terminal, via the network, to display the report information indicating parameter information, the report information indicating a state of the sperm of each of the plurality of moving images which has been selected and analyzed by the embryologist based on the status, the report information indicating overall findings of the embryologist for multiple pieces of the parameter information.

2. A reporting system comprising:
a reporting device;
a user terminal; and
an embryologist terminal, wherein
the reporting device includes
a moving image receiving unit configured to receive, from the user terminal, via a network, a moving image obtained by imaging sperm of a user,
a moving image processing unit configured to cause the embryologist terminal, via the network, to display the moving image received by the moving image receiving unit,
a report information receiving unit configured to receive, from the embryologist terminal, via the network, report information indicating a result obtained by analyzing the sperm of the user by an embryologist, based on the moving image displayed on the embryologist terminal, and
a report information processing unit configured to cause the user terminal, via the network, to display the report information received by the report information receiving unit,
the user terminal includes
a moving image acquisition unit configured to acquire the moving image, wherein the moving image acquisition unit is detachably attached to an observation loupe to magnify the moving image,
a moving image transmission unit configured to transmit the moving image acquired by the moving image acquisition unit to the reporting device, and
a first display unit configured to display the report information, and
the embryologist terminal includes
a second display unit configured to display the moving image,
a report information acquisition unit configured to acquire the report information input by the embryologist, based on the moving image displayed on the second display unit, and
a report information transmission unit configured to transmit the report information acquired by the report information acquisition unit to the reporting device,
wherein
the moving image receiving unit is configured to receive, from the user terminal, via the network, a plurality of moving images with different collection dates of the sperm with respect to one piece of identification information of the user,
the moving image processing unit is configured to:
determine, for each of the plurality of moving images, a status based on whether analysis is performed on each of the plurality of moving images;
cause the embryologist terminal, via the network, to display the status for each of the plurality of moving images; and
update, for at least one of the plurality of moving images, the status from "unsupported" to "being supported," based on selection of the at least one of the plurality of moving images by the embryologist, and
the report information processing unit is configured to cause the user terminal, via the network, to display the report information indicating parameter information, the report information indicating a state of the sperm of each of the plurality of moving images which has been selected and analyzed by the embryologist based on the status, the report information indicating overall findings of the embryologist for multiple pieces of the parameter information.

* * * * *